US00PP22329P2

(12) United States Plant Patent
Wood

(10) Patent No.: US PP22,329 P2
(45) Date of Patent: Dec. 13, 2011

(54) ***HYDRANGEA* PLANT NAMED 'BERNER'**

(50) Latin Name: *Hydrangea macrophylla*
Varietal Denomination: Berner

(75) Inventor: Timothy D. Wood, Spring Lake, MI (US)

(73) Assignee: Spring Meadow Nursery, Inc., Grand Haven, MI (US)

( * ) Notice: Subject to any disclaimer, the term of this patent is extended or adjusted under 35 U.S.C. 154(b) by 0 days.

(21) Appl. No.: 12/807,828

(22) Filed: Sep. 14, 2010

(51) Int. Cl.
*A01H 5/00* (2006.01)

(52) U.S. Cl. ..... Plt./250

(58) Field of Classification Search ..... Plt./250
See application file for complete search history.

*Primary Examiner* — Annette Para
(74) *Attorney, Agent, or Firm* — C. A. Whealy

(57) ABSTRACT

A new and distinct cultivar of *Hydrangea* plant named 'Berner', characterized by its upright and mounded plant habit; strong and sturdy stems; dark green-colored leaves; large mophead-type inflorescences with numerous dark pink-colored sterile flowers; and reblooming habit.

2 Drawing Sheets

Botanical designation: *Hydrangea macrophylla.*
Cultivar denomination: 'BERNER'.

BACKGROUND OF THE INVENTION

The present invention relates to a new and distinct cultivar of *Hydrangea* plant, botanically known as *Hydrangea macrophylla* and hereinafter referred to by the name 'Berner'.

The new *Hydrangea* plant is a product of a planned breeding program conducted by the Inventor in Grand Haven, Mich. The objective of the breeding program was to develop new reblooming *Hydrangea* plants with strong stems and attractive foliage and flower coloration.

The new *Hydrangea* plant originated from an open-pollination in July, 2003 of the *Hydrangea macrophylla* 'Bailmer', disclosed in U.S. Plant Pat. No. 15,298, as the female, or seed parent and an unknown selection of *Hydrangea macrophylla* as the male, or pollen, parent. The new *Hydrangea* plant was discovered and selected by the Inventor in May, 2005 as a flowering plant within the progeny of the stated open-pollination in a controlled environment in Grand Haven, Mich.

Asexual reproduction of the new cultivar by softwood cuttings in a controlled environment in Grand Haven, Mich. since June, 2005 has shown that the unique features of this new *Hydrangea* plant are stable and reproduced true to type in successive generations of asexual reproduction.

SUMMARY OF THE INVENTION

Plants of the new *Hydrangea* have not been observed under all possible environmental conditions. The phenotype may vary somewhat with variations in environment and cultural practices such as temperature and light intensity without, however, any variance in genotype.

The following traits have been repeatedly observed and are determined to be the unique characteristics of 'Berner'. These characteristics in combination distinguish 'Berner' as a new and distinct cultivar of *Hydrangea* plant:

1. Upright and mounded plant habit.
2. Strong and sturdy stems.
3. Dark green-colored leaves.

4. Large mophead-type inflorescences with numerous dark pink-colored sterile flowers.
5. Reblooming habit.

Plants of the new *Hydrangea* differ from plants of the female parent, 'Bailmer', in the following characteristics:

1. Plants of the new *Hydrangea* have thicker, darker and glossier leaves than plants of 'Bailmer'.
2. Plants of the new *Hydrangea* have larger inflorescences than plants of 'Bailmer'.
3. Plants of the new *Hydrangea* have more intense and darker pink-colored flowers than plants of 'Bailmer'.

Plants of the new *Hydrangea* can be compared to plants of *Hydrangea macrophylla* 'Robert', disclosed in U.S. Plant Pat. No. 20,020. In side-by-side comparisons, plants of the new *Hydrangea* differ from plants of 'Robert' in the following characteristics:

1. Plants of the new *Hydrangea* have stronger stems than plants of 'Robert'.
2. Plants of the new *Hydrangea* have larger inflorescences than plants of 'Robert'.

BRIEF DESCRIPTION OF THE PHOTOGRAPHS

The accompanying colored photographs illustrate the unique appearance of the new *Hydrangea* plant showing the colors as true as it is reasonably possible to obtain in colored reproductions of this type. Colors in the photographs may differ from the color values cited in the detailed botanical description which accurately describe the colors of the new *Hydrangea* plant. The photograph on the first sheet comprises a side perspective view of a typical flowering plant of 'Berner' grown in an outdoor nursery. The photograph on the second sheet is a close-up view of a typical inflorescence of 'Berner'.

DETAILED BOTANICAL DESCRIPTION

Plants used for the aforementioned photographs and the following description were grown during the spring and summer in a 30% shadehouse in Grand Haven, Mich. and under conditions which closely approximate commercial *Hydrangea* production conditions. Plants of the new *Hydrangea* were three years old when the photographs and description were taken. In the following description, color references are made to The Royal Horticultural Society Colour Chart, 2001 Edition, except where general terms of ordinary dictionary significance are used.

Botanical description: *Hydrangea macrophylla* 'Berner'.

Parentage:

*Female, or seed, parent.*—*Hydrangea macrophylla* 'Bailmer', disclosed in U.S. Plant Pat. No. 15,298.

*Male, or pollen, parent.*—Unknown selection of *Hydrangea macrophylla,* not patented.

Propagation:

*Type cutting.*—By softwood cuttings.

*Time to initiate roots, summer.*—About ten days at temperatures of about 27° C.

*Time to produce a rooted young plant, summer.*—About three months at temperatures of about 27° C.

*Root description.*—Fine and thick, fibrous; white and brown in color.

*Rooting habit.*—Freely branching; dense.

Plant description:

*Plant form and growth habit.*—Perennial deciduous shrub; upright and mounded plant habit; broadly inverted triangle; strong and sturdy lateral branches; freely branching habit; vigorous growth habit.

*Plant height.*—About 60 cm.

*Plant diameter or area of spread.*—About 60 cm.

*Lateral branches.*—Length: About 38 cm. Diameter: About 7 mm. Internode length: About 6.3 cm. Texture: Smooth, glabrous. Strength: Strong, sturdy. Color: Close to 144A with random blotches, close to 59A.

Foliage description:

*Arrangement.*—Opposite, simple.

*Length.*—About 19 cm.

*Width.*—About 11 cm.

*Shape.*—Ovate.

*Apex.*—Acute to acuminate.

*Base.*—Cuneate to attenuate.

*Margin.*—Serrate.

*Texture, upper and lower surfaces.*—Smooth, glabrous; rugose.

*Venation pattern.*—Pinnate.

*Color.*—Developing leaves, upper surface: Close to 141B. Developing leaves, lower surface: Close to 146C. Fully expanded leaves, upper surface: Close to 147A; venation, close to 144A. Fully expanded leaves, lower surface: Close to 148B; venation, close to 148B.

*Petioles.*—Length: About 2.9 cm. Diameter: About 4 mm. Texture, upper and lower surfaces: Smooth, glabrous. Color, upper and lower surfaces: Close to 144A.

Flower description:

*Flower type and habit.*—Single sterile and fertile flowers arranged on large terminal and axillary mophead-type cymes; flowers face upright or outwardly.

*Fragrance.*—None detected.

*Natural flowering season.*—Continuous flowering throughout the summer, June until first frost, in Grand Haven, Mich.; plants continue to rebloom during this period.

*Flower longevity, fertile flowers.*—Flowers last about ten days on the plant; flowers not persistent.

*Flower longevity, sterile flowers.*—Flowers last about 4.5 months on the plant; flowers persistent.

*Quantity of flowers.*—Freely flowering; about 20 fertile flowers and about 183 sterile flowers per inflorescence.

*Inflorescence height.*—About 13 cm.

*Inflorescence diameter.*—About 24 cm.

*Flower diameter, fertile flowers.*—About 5 mm.

*Flower depth (height), fertile flowers.*—About 4 mm.

*Flower diameter, sterile flowers.*—About 6 cm.

*Flower depth (height), sterile flowers.*—About 2.5 cm.

*Flower buds, fertile and sterile flowers.*—Length: About 3 mm. Diameter: About 5 mm. Shape: Globular. Color: Close to 62C.

*Petals, fertile flowers only.*—Arrangement: Five in a single whorl. Length: About 3.5 mm. Width: About 2.5 mm. Shape: Elliptical. Apex: Acute. Base: Attenuate. Margin: Entire. Texture, upper and lower surfaces: Smooth, glabrous. Color: When opening, upper and lower surfaces: Close to 97A. Fully opened, upper and lower surfaces: Close to 97A.

*Sepals, fertile flowers.*—Quantity per flower: Five in a single whorl. Length: About 1 mm to 2 mm. Width: About 1 mm. Shape: Ovate. Apex: Acute. Base: Fused. Margin: Entire. Texture, upper and lower surfaces: Smooth, glabrous. Color, upper and lower surfaces: Close to 145C.

*Sepals, sterile flowers.*—Quantity per flower: About four to seven in a single whorl. Length: About 3 cm. Width: About 4 cm. Shape: Reniform to broadly elliptical. Apex: Obtuse. Base: Broadly obtuse to attenuate. Margin: Serrate. Texture, upper and lower surfaces: Smooth, glabrous. Color: When opening, upper and lower surfaces: Close to 73B to 73C. Fully opened, upper and lower surfaces: Close to 73B to 73C.

*Peduncles, fertile and sterile flowers.*—Angle: Erect to about 45° from vertical. Strength: Strong, sturdy. Length: About 13 cm. Diameter: About 5 mm. Texture: Slightly pubescent. Color: Close to 144A with random blotches, close to 59A.

*Pedicels, fertile flowers.*—Angle: Erect to about 40° from vertical. Strength: Moderately strong. Length: About 5 mm. Diameter: About 1 mm. Texture: Pubescent. Color: Close to 73D.

*Pedicels, sterile flowers.*—Angle: Erect to about 90° from vertical. Strength: Strong. Length: About 3.5 cm. Diameter: About 2 mm. Texture: Pubescent. Color: Close to 73A.

*Reproductive organs, fertile flowers only.*—Stamens: Quantity per flower: About eight. Anther shape: Oblong. Anther length: About 1 mm. Anther color: Close to 143B. Pollen amount: Scarce. Pollen color: Close to 202D. Pistils: Pistil quantity per flower: About three. Pistil length: About 1 mm. Stigma shape: Oblong. Stigma color: Close to 155A. Style length: About 0.5 mm. Style color: Close to 155A. Ovary color: Close to 144D.

*Fruits.*—Type: Capsule. Length: About 3 mm. Diameter: About 2 mm. Color: Brown.

*Seeds.*—Quantity per inflorescence: Numerous. Size: Less than 0.1 mm by less than 0.1 mm. Color: Brown.

Disease/pest resistance: Plants of the new *Hydrangea* have been observed to be resistant to mildew. Plants of the new

*Hydrangea* have not been observed to be resistant to pests or other pathogens common to *Hydrangea*.

Temperature tolerance: Plants of the new *Hydrangea* have been shown to be tolerant to temperatures ranging from about −20° C. to about 38° C.

It is claimed:

1. A new and distinct *Hydrangea* plant named 'Berner' as illustrated and described.

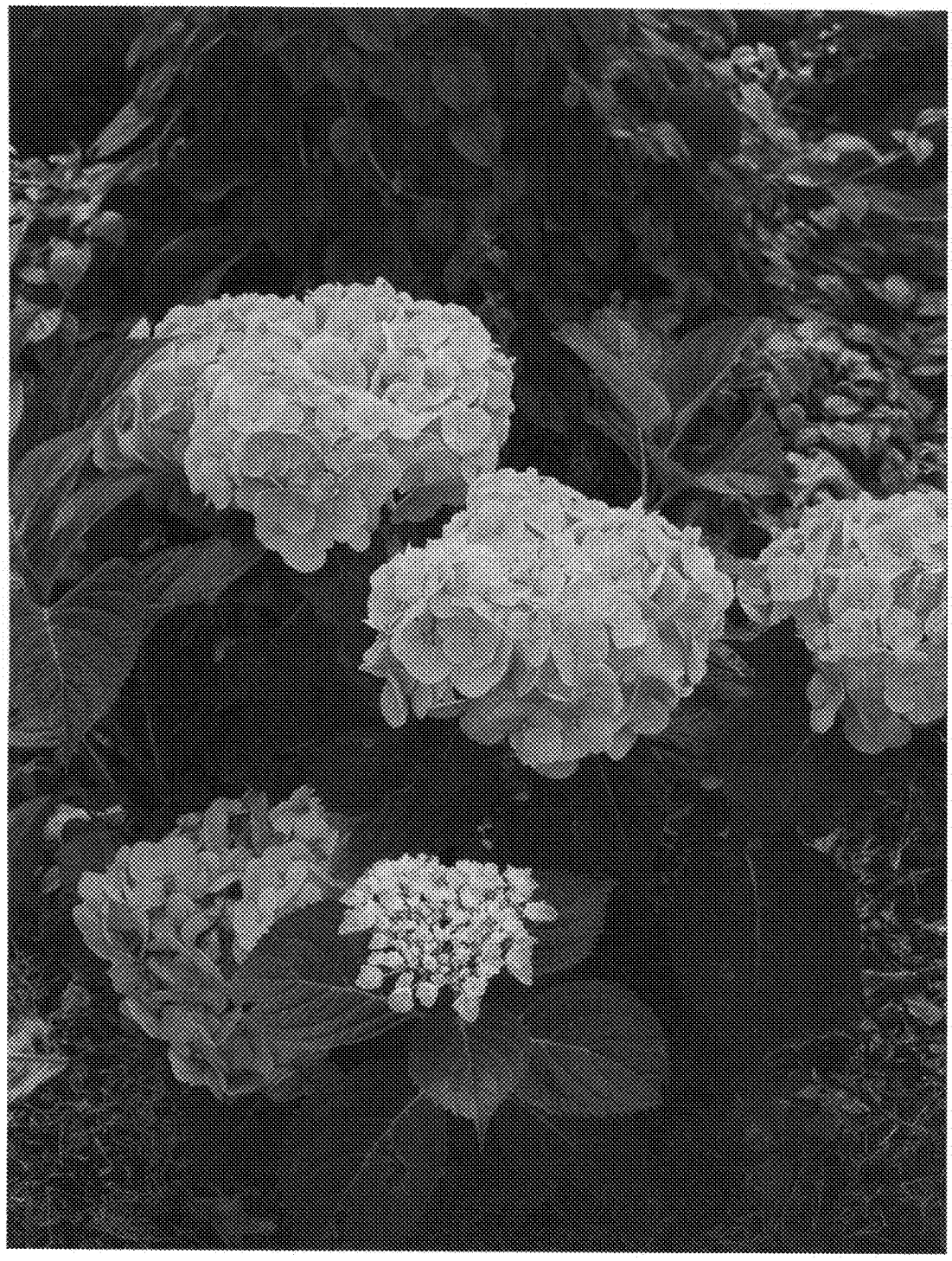

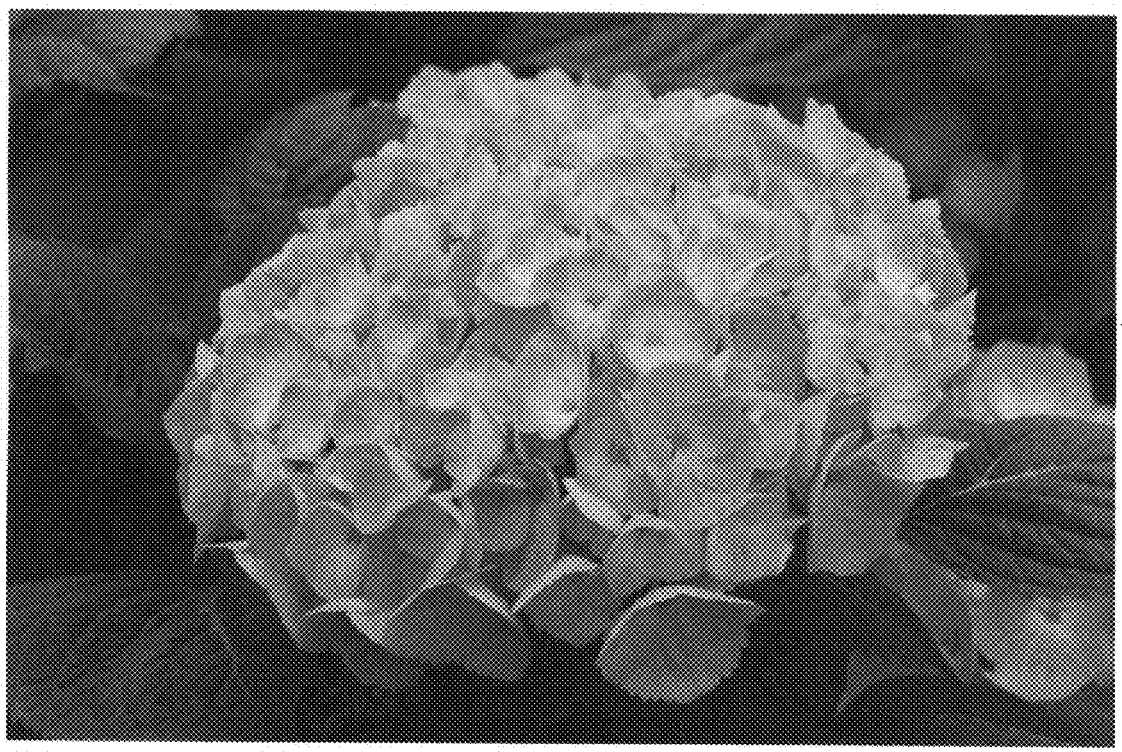

* * * * *